United States Patent [19]

Menger

[11] Patent Number: 5,391,726

[45] Date of Patent: Feb. 21, 1995

[54] PREPARATION OF GIANT RING COMPOUNDS

[75] Inventor: Fredric M. Menger, Decatur, Ga.

[73] Assignee: The Dow Chemical Company, Midland, Mich.

[21] Appl. No.: 875,952

[22] Filed: Apr. 30, 1992

[51] Int. Cl.$^6$ .................... C08B 37/00; C07D 321/00
[52] U.S. Cl. ..................... 536/54; 547/200; 547/228; 547/347; 547/352
[58] Field of Search ............... 549/218, 219, 220, 228, 549/200, 347, 352

[56] References Cited

PUBLICATIONS

Angew. Chem. Int. Ed. Engl., 1992, 31, No. 11, pp. 1492–1493.
Herbert et al., *J. Org. Chem.*, 57, 1777–1783, Mar. 12, 1992; "A New Reagent for the Removal of the 4-Methoxybenzyl Ether: Application to the Synthesis of Unusual Macrocyclic and Bolaform Phosphatidylcholines".
McMurry et al., *J. Am. Chem. Soc.*, 112, 6942–6949, Sep. 12, 1990; "Total Synthesis of (±)-Isolobophytolide and (±)-Crassin by Titanium-Induced Carbonyl Coupling".
Guivisdalsky et al., *J. Org. Chem.*, 54, 4637–4642, Sep. 15, 1989; "Regiospecific Opening of Glycidyl Derivatives Mediated by Boron Trifluoride. Asymmetric Synthesis of Ether-Linked Phospholipids".
Bhatia et al., *J. Org. Chem.*, 53, 5034–5039, Oct. 14, 1988; "Stereospecific Synthesis of Ether and Thioether Phospholipids. The Use of L-Glyceric Acid as a Chiral Phospholipid Precursor".
Yamauchi et al., *J. Chem. Soc., Chem. Commun.*, 445–446, Mar. 15, 1988; "Modification of Neutral (Isoelectric) Liposomes to Anionic Liposomes by Phospholipase A$_2$: The Use of Macrocyclic 1,2-Dotriacontanedioyl-sn-glycero-3-phosphocholine".
Macaulay, *J. Org. Chem.*, 45, 734–735, Feb. 15, 1980; "Isomerization of Internal Triple Bonds of Alkyn-1-ols with Sodium Hydride in 1,3-Diaminopropane".
Moss et al., *Langmuir*, vol. 7, No. 11, 2415–2418, Nov. 1991; "Dynamics of a Bolaamphiphilic Lipid in a Bilayer Liposome".
Moss et al., *Tetrahedron Letters*, vol. 11, No. 52, 7559–7562, Dec. 17, 1990; "Dynamics of Liposomes Constructed From Phytanyl Lipids".
Moss et al., *J. Am. Chem. Soc.*, 112, 6391–6392, Aug. 15, 1990; "Relation of Surfactant Monomer Structure to Flip-Flop Dynamics in Surface-Differentiated Synthetic Bilayer Membranes".
Boger et al., *J. Am. Chem. Soc.*, 112, 4008–4011, May 9, 1990; "Intramolecular Acyl Radical-Alkene Addition Reactions: Macrocyclization Reactions".
Yamauchi et al., *J. Am. Chem. Soc.*, 112, 3188–3191, Apr. 11, 1990; "Archaebacterial Lipid Models. Highly Thermostable Membranes from 1,1'-(1,32-Dotriacontamethylene)-bis(2-phytanyl-sn-glycero-3-phosphocholine".
de Rosa et al., *J.C.S. Chem. Comm.*, 15, 514–515, Aug. 3, 1977; "Lipid Structures in the Caldariella Group of Extreme Thermoacidophile Bacteria".
Yamauchi et al., *Biochimica et Biophysica Acta*, 1003, 151–160, Jun. 8, 1989; "Peculiar Membrane Morphologies of Archaebacterial Lipid Models: 1,1'-polymethylenebis(2-alkyl-sn-glycero-3-phosphocholine)".
de Rosa et al., *J.C.S. Chem. Comm.*, 12, 543–544, Jun. 12, 1974; "Cyclic Diether Lipids from Very Thermophilic Acidophilic Bacteria".
Derwent Publication, 90238821/31, U.S. Sec. of Navy, (U.S. 7442-961-A), Nov. 29, 1989.

*Primary Examiner*—G. S. Kishore
*Assistant Examiner*—Peter F. Kulkosky
*Attorney, Agent, or Firm*—Duane C. Ulmer

[57] ABSTRACT

The invention concenrs giant ring compounds containing about 20 to about 160 atoms in the backbone of the ring and methods for preparing the giant ring compounds.

2 Claims, No Drawings

PREPARATION OF GIANT RING COMPOUNDS

GOVERNMENT INTEREST

This invention was made in part with Government support under Grant GM-21457 by the National Institutes of Health. The Government has certain rights to this invention.

BACKGROUND OF THE INVENTION

The present invention relates to the composition of giant ring compounds and methods for preparing the giant ring compounds.

Phospholipids, a major constituent of biological membranes, typically possess two chains of 14–18 carbons each of which are linked to the glycerol backbone by means of ester functionalities. Such compounds are stable at ambient temperature and neutral pH, but readily decompose at: elevated temperatures; in highly acidic media; and/or in enzymatic reactions catalyzed by esterases. Furthermore, since the hydrophobic chains are connected only at one end, they have a certain amount of freedom within the membrane bilayer to wiggle, bend, and interdigitate.

It has been observed that thermophilic archaebacteria are fully functional at temperatures up to 90° C. and some at external pH values as low as 0.5. The ability of these bacteria to thrive under such adverse conditions is believed to be due in part to the unique lipids present in the plasma membrane. Two of the unique features of lipids of the plasma membrane being that they are macrocyclic and have a complete absence of ester linkages. The lack of ester linkages results in enhanced stability of such lipids to enzymatic hydrolysis by esterases, in addition to the temperature and pH stability. The cyclic nature of the lipids from archaebacteria is characterized as long isoprenoid chains bound through ether linkages to two polar heads; the two polar heads being either two glycerols or one glycerol and one nonitol. See, for example, Rosa et al., *J.C.S. Chem. Comm.* 514–515 (1977); Yamauchi et al., *Biochim. Biophy. Acta* 1003, 151–160 (1989); Yamauchi et al., *J. Am. Chem. Soc.* 112, 3188–3191 (1990).

Due to the unique properties of the lipids from archaebacteria, there is interest in using such lipids to form thermal, enzymatic, and pH stable membranes as liposomes for drug and pesticide delivery, for use in cleaning products, and for use in high performance fluids such as high temperature lubricants. However, it is difficult to obtain the bacterial lipids from natural sources and chemical synthesis is not an easy task.

Synthetic procedures for making macrocyclic rings having 12 to 20 atoms in the backbone of the ring include a method for preparing ether-linked phospholipids based on regiospecific opening of glycidyl derivatives mediated by boron trifluoride as described by Guivisdalsky et al. *J. Org. Chem.* 54, 4637–4642 (1989).

Yamauchi et al. *J. Am. Chem. Soc.* 112, 3188–3191 (1990) describe the synthesis of 1,1'-(1,32-dotriacontamethylene)-bis-(2-phytanyl-sn-glycero-3-phosphocholine) as a model to study the macrocyclic lipids.

McMurry et al. *J. Am. Chem. Soc.* 112, 6942–6949 (1990) describe a process for forming macrocyclic diols having a 14-membered carbocyclic ring. None of the procedures currently used have been effective in preparing macrocyclic lipids having greater than 12 to 20 atoms in the ring in significant yields.

It would therefore be advantageous to synthetically produce macrocycles having greater than 20 atoms in the backbone of the ring whereby the hydrophobic chains are linked to a polar backbone. It would also be advantageous to have macrocycles of greater than 20 atoms where the hydrophobic chains are linked to a glycerol backbone by means of ether functionalities. Such macrocycles have enhanced thermal stability, chemical stability, photolytic stability and enzymatic stability compared to previously synthesized cyclic stuctures which contain ester linkages.

SUMMARY OF THE INVENTION

The present invention concerns giant ring compounds of Formula I

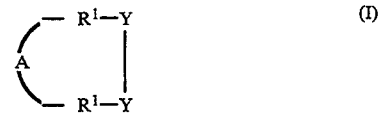

(I)

where A is a hydrophilic moiety; each $R^1$ is independently a $C_8$–$C_{40}$ backbone alkylene, alkenylene, alkynylene, alkadiynylene, $(-OCH_2CH_2-)_n$ or $(-OCHR^5CHR^5-)_n$; where each $R^5$ is independently H or a $C_1$–$C_3$ alkyl; n is an integer from 8 to 20; and each Y is independently $-C\equiv C-$, $-CH=CH-$, or $-CH_2CH_2-$.

The present invention also concerns giant ring compounds of Formula II

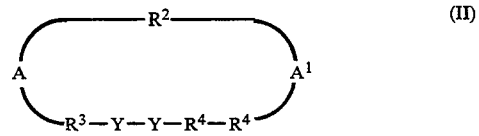

(II)

where A and $A^1$ are each independently a hydrophilic moiety;

$R^2$ is a $C_{20}$–$C_{80}$ backbone alkylene, alkenylene, alkynylene, alkadiynylene, $(-OCH_2CH_2-)_n$, or $(-OCHR^5CHR^5-)_n$;

each $R^5$ independently is H or $C_1$–$C_3$ alkyl;

each Y is independently $-C\equiv C-$, $-CH=CH-$, or $-CH_2CH_2-$;

$R^3$ and $R^4$ are each independently a $C_8$–$C_{40}$ backbone alkylene, alkenylene, alkynylene, alkadiynylene, $(-OCH_2CH_2-)_n$ or $(-OCHR^5CHR^5-)_n$; and n is an integer of from 8 to 20.

In another aspect of the invention, a process is provided for preparing giant ring compounds having from about 20 to about 160 atoms in the backbone of the ring comprising contacting a copper ion with one or more compounds having at least two terminal acetylenic groups under oxidative conditions to produce coupling of terminal acetylene groups to form a giant ring compound.

The synthetic method of this invention enables preparation of lipids with straight chains, as well as unlimited variety of chains with different types of branches and substituents versus the lipids isolated from thermophilic archaebacteria having hydrocarbon chains branched in a strictly defined manner.

DETAILED DESCRIPTION OF THE INVENTION

As used herein the term "giant ring" means a cyclic compound having 20 to about 160 atoms in the backbone of the ring. The term "liposome" means a vesicle which contains a liquid and the walls of which are formed from lipids. The term "copper" means the cuprous form. The terms "alkyl", "alkane", "alkene" and "alkyne" when used herein mean branched and/or unbranched hydrocarbon groups having the indicated unsaturation at one or more occurance. The term "terminal acetylenic group" means $-C{\equiv}CT$ where T is hydrogen or a hydrolyzable group such as a halogen or organosiloxane (i.e. $(R^6)_3Si$ where $R^6$ is an alkyl or alkoxy group having from 1 to 5 carbon atoms). The term "acetylenic compound" means a compound that has at least two terminal acetylenic groups. The term "hydrophilic" means a moiety which is polar or ionic in nature.

The process of the present invention allows synthesis of giant ring compounds having a polar moiety and a hydrophobic moiety as represented by Formula I. The process of the present invention can also be utilized to produce giant rings with two polar groups (bipolar) separated by a hydrophobic chain as represented by Formula II.

It has been found that giant rings can be prepared by contacting one or more compounds having at least two terminal acetylenic groups with copper in an organic solvent under oxidative conditions to allow coupling of at least two of the terminal acetylene groups. This procedure is a modification of what is known as a Glaser reaction which uses copper, ammonia or ammounium ion and oxygen in the reaction to couple alkynes. The Glaser reaction has previously been found to be unsatisfactory for cyclic coupling of two alkyne molecules. See, for example, March, *Advanced Organic Chemistry*, John-Wiley & Sons, Inc., p. 640 (1985).

Preferably, compounds for use in the process of the present invention to form the giant rings are acetylenic compounds represented by Formulae (III) and (IV):

$$A(R^1C{\equiv}CT)_2 \quad (III)$$

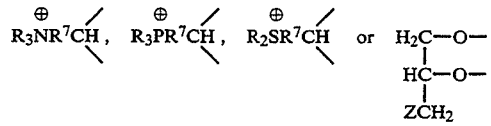  (IV)

wherein A and $A^1$ are hydrophilic groups; and $R^1, R^2, R^3, R^4$ and T are all as previously defined Examples of polar compounds represented by A and $A^1$ include

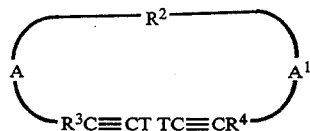

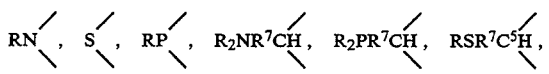

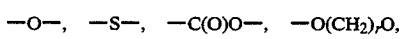

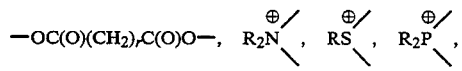

where each R independently is hydrogen or a $C_1$–$C_8$ alkyl;

$R^7$ is $(CH_2)_q$ where q is an integer from 1 to 4;

$R^8$ is hydrogen or a $C_1$–$C_8$ alkyl;

r is an integer from 1 to 4; and each Z is independently $-OH$, $C_1$–$C_8$ alkoxy, O-benzyl, O-phosphate, O-glucose-sulfate, or ZH=W where W is a phosphatidylethanolamine, phosphatidylserine, phosphatidyl choline, phosphatidyl inositol, phosphatidyl ethanol trimethylamine, phospahtidic acid or a sugar moiety. A sugar moiety being a substituted or nonsubstituted mono, di, or trisaccharide, the substituted group being a phosphoryl or sulfonyl moiety.

Thus acetylenic compounds of the general formulae

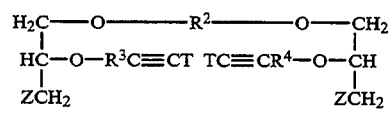

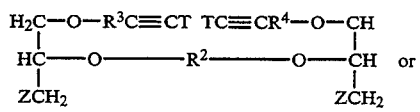

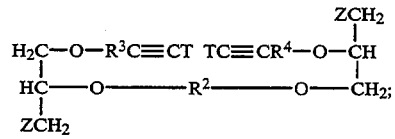

wherein $R^2, R^3, R^4$ and Z are as defined before, can be used in the process of the present invention to form giant rings.

The preferred compounds for use in the present invention to produce giant rings containing one polar head group are compounds of Formula III where A is

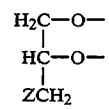

where each Z is independently a hydroxyl, O-benzyl, phosphate, glucose sulfate, or phosphatidyl cholinyl;

$R^1$ is a $C_{12}$–$C_{16}$ alkylene; and

T is hydrogen.

The preferred compounds for use in the present invention to form giant rings containing two polar groups are compound of Formula IV where A equals $A^1$; $R^3$ equals $R^4$; A is

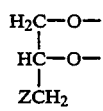

where Z is independently at each occurrence a hydroxyl, O-benzyl, phosphate, glucose sulfate, or phosphatidyl cholinyl;

$R_2$ is a $C_{28}$–$C_{36}$ alkylene;

$R^3$ is a $C_{12}$–$C_{16}$ alkylene; and

T is hydrogen.

The components (acetylenic compound and copper ion) of the reaction are generally dissolved in an organic solvent. The organic solvent in which the reaction for formation of the giant rings is conducted is not crucial to the process o the present invention. Any organic solvent in which the acetylenic compound is soluble and which does not have a detrimental effect on the coupling process can be used. Examples of suitable organic solvents include tetrahydrofuran, xylene, hexane, benzene, carbon tetrachloride, cyclohexane, cyclopentane, toluene, dioxane, methylene chloride, chloroform, acetonitrile, and the like.

The concentration of acetylenic compound in the organic solvent will be about 0.1 to about 500 millimolar (mM), preferably about 0.5 (mM) to about 100 mM and will be dependent upon the solvent and molecular weight of the acetylenic compound. The concentration of acetylenic compound to use in the reaction can be determined by those of ordinary skill in the art.

Copper (I), usually in the form of a copper salt, is added to the reaction mixture at a molar excess to the acetylenic compound. The amount of excess molar equivalents of copper to acetylenic compound is not crucial to the reaction and is preferably less than about 10:1, and more preferably less than about 5:1. Examples of copper salts which can be used in the process of the present invention include copper sulfate, copper halides (including copper chloride), copper nitrate, copper salts of carboxylic acids in the homologous series from formic acid to decainoic acid, copper salts of polybasic acids in the series from oxalic acid to suberic acid and copper salts of hydrocarboxylic acids including glycols, lactic, tartaric, malic and citric acids. Further specific examples include copper benzoate, copper gluconate, copper glycerophosphate, copper propionate and copper salicylate.

To facilitate coupling of the terminal acetylenic groups of the acetylenic compounds to form a giant ring, a base is added to complex with the copper ion. Preferably the base is an organic amine base such as di- or triethylamine, N,N,N'-trimethylethylenediamine or N,N,N'N'-tetramethylethylenediamine (TMEDA). More preferably the base is TMEDA.

An additional component in the reaction mixture for the process of the present invention is oxygen. Oxygen can be added to the reaction by passing a gaseous stream of oxygen or a gaseous stream which contains oxygen through the reaction mixture. For simplicity, oxygen can be supplied by passing a stream of oxygen through the reaction mixture utilizing conventional equipment and techniques known to those of ordinary skill in the art.

Alternatively, oxygen can be supplied to the reaction mixture by means of an oxidizing agent. Exemplary of such oxidizing agents are permanganate and hydrogen peroxide. The oxidizing agent is supplied in a molar excess to the diacetylenic compound.

The reaction for coupling the two acetylenic groups is run at a temperature of about 100° C. to about 200° C., preferably the reaction is conducted at a temperature of about 120° C. to about 175° C.

The precursors to form the acetylenic compounds which can be coupled to form the giant ring compounds of the present invention are commercially available or can be prepared using standard procedures known in the art. For example, a general synthetic approach where $R^1$ is a linear alkyl, A is a glycerol derivative and T is a hydrogen is given in the following Scheme 1.

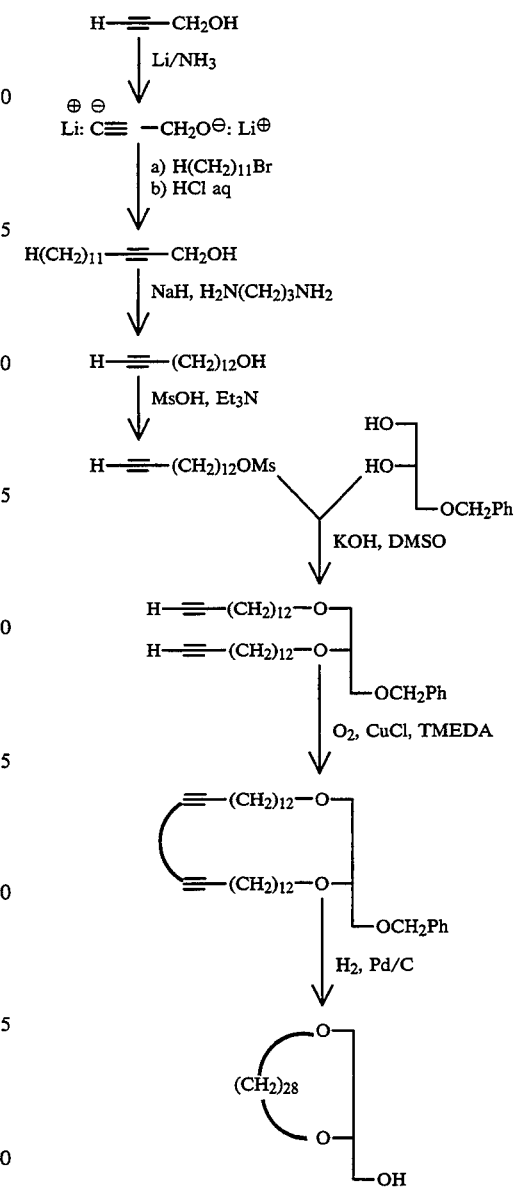

Propargyl alcohol is reacted with lithium in liquid ammonia to form the dilithium salt of propargylol. The salt is then reacted with a primary alkyl halide and then dilute acid is added, (bromoundecane and hydrochloric acid are given in the scheme), to form the 2-alkyn-1-ol. The alcohol undergoes isomerization in sodium hydride/1,3-propylenediamine to form an alkyn-1-ol having a terminal acetylenic group. The hydroxyl group of the resulting alkynol is converted to the mesyl derivative by reacting the alkynol with methanesulfonic acid in triethylamine (Et$_3$N) to form the alkynyl mesylate. The alkynyl mesylate can then be reacted with commercially available compounds, such as dl-α-benzyl glycerol indicated in scheme 1, in the presence of a strong base, such as potassium or sodium hydroxide, and a polar solvent, such as dimethyl sulfoxide (DMSO), to form a 1,2-di-O-alkynyl-3-O-benzylglycerol. This compound is then converted to a giant ring by using the process of the present invention.

The removal of the benzyl protecting group and conversion to a lipid may be accomplished by standard procedures known to those of ordinary skill in the art. For example, the benzyl group can be removed by catalytic hydrogenation or with dimethyl bromide at −50° C. to −100° C. A phosphoryl group, such as phophatidylcholinyl, can then be added by use of various phosphoryl chlorides in the presence of an amine base.

Other acetylenic compounds for use in the present invention can be prepared by reacting an alkylamine (i.e. QNH$_2$, where Q is a C$_1$-C$_9$ linear or branched alkyl) with about 1 equivalent of an haloalkyne (i.e., Br(CH$_2$)$_p$—C≡CH, where p is 8 to 40 ) in base to form an N-alkyl-N-alkynylamine (QNH(CH$_2$)$_p$C≡CH). The N-alkyl-N-alkynylamine is then reacted with about one equivalent of an haloalkyne to form a N-alkyl-N,N-dialkynylamine. The resulting N-alkyl-N,N-dialkynylamine can then be converted to a macrocycle by using the process of the present invention. The amine can then be converted to a quaternary amine by known procedures in the art. Similar type reactions can be done to produce the thio-and phosphoryl diacetylenic compounds used for forming macrocycles.

Compounds containing two polar heads can also be prepared using standard techniques known in the art. For example, a general synthetic approach where R$^2$ is dotriacontylene, A and A$^1$ are

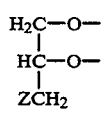

Z is hydroxy, T is hydrogen, and R$^3$ and R$^4$ are 1-hexadec-15-ynyl groups is given in the following Scheme 2

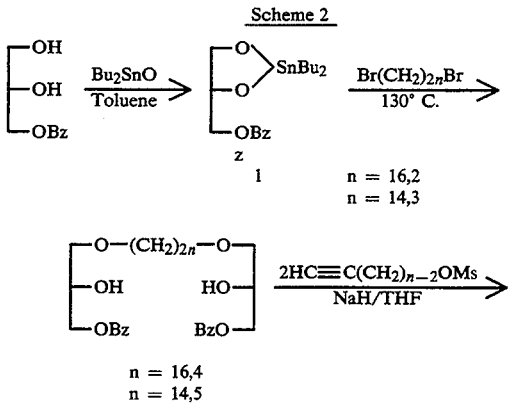

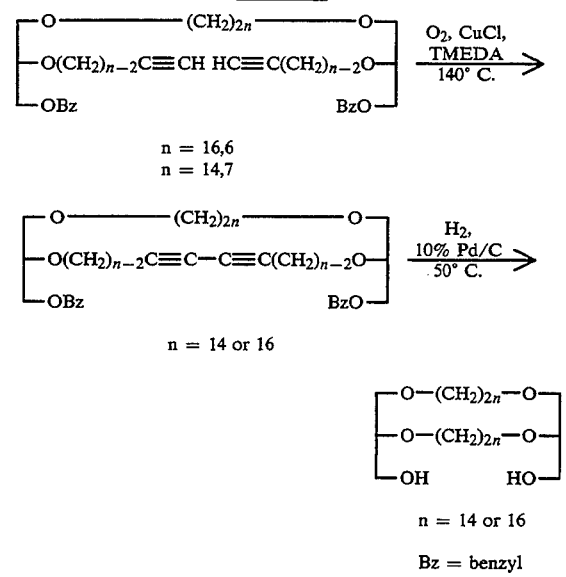

A 1,1'—C$_{32}$—linked compound (compound 4 of Scheme 2) is produced by reacting 1-O, 2-O-(dibutyl)-stannylene-3-O-benzyl-glycerol with 1,32-dibromotriacontane. Compound 4 is then reacted with a alkynyl mesylate to produce the 2,2' -diether. By utilizing the process of the present invention this acyclic tetraether is converted to a giant ring, followed by hydrogenation of the acetylenic groups if desired.

The giant rings can be recovered from the reaction mixture using standard techniques known in the art.

The invention will be further clarified by a consideration of the following examples, which are intended to be purely exemplary of the present invention.

Structural identification of compounds is indicated by reference to the compound numbers in scheme 2 or to the compound numbers in the examples.

EXAMPLE A 1,1'-Dotriacontamethylenebis(2-(15-hexadecynyl)-3-benzyl-glycerol)(compound 6)

A solution of compound (4)(0.85 g, 1.1 mmol) in dry THF (10 mL) was stirred with sodium hydride (80 percent, 0.13 g, 4.2 mmol, 4 equiv.) for 2 hours under nitrogen at room temperature. To the resulting sodium alkoxide solution was added 15-hexadecyn-1-yl methanesulfonate (0.83 g, 2.6 mmol, 2.5 equiv.) and the mixture was refluxed for two days. After cooling, the solution was filtered through a short alumina column and then concentrated. The residue was purified by silica gel column, eluting with hexane-ethyl acetate (10:1 v/v) (monitored by TLC, with hexane-ethyl acetate 7:1 v/v as the solvent system) to give 6 (0.80 g, 64% yield).

EXAMPLE B 1,1'-Octacosamethylenebis(2-(13-tetradecynyl)-3-benzyl-glycerol) (compound 7)

Following the procedure of Example A using 1.02 g (1.35 mmol) of 5, sodium hydride (80 percent, 0.16 g, 5.4 mmol, 4.0 equiv.), and replacing the 15-hexadecyn-1-yl-methanesulfonate with 13-tetradecyn-1-yl-methanesulfonate (0.97 g, 3.38 mmol, 2.5 equiv.). A 61 percent yield of 7 (0.94 g) was obtained.

Example 1

Formation of a 40 atom diether giant ring

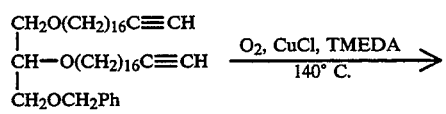

(8)

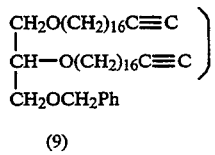

(9)

To a three-neck, 500 mL round bottom flask containing 200 mL of xylene and equipped with a magnetic stirring bar, a condenser, a rubber stopper with a glass tube, and a septum were added CuCl (0.37 g, 3.8 mmol, 2.5 equiv.) and N,N,N',N'-tetramethylethylenediamine (TMEDA)(0.60 mL, 4.0 mmol, 2.6 equiv.). The solution was heated to 140° C. in an oil bath, while oxygen was gently bubbled into it through the glass tube. During the heating period, the solution first became light green, then dark olive-green. When the temperature reached 125°–130° C., a dark xylene-insoluble oily substance settled along the inner surface of the reaction flask. As the temperature continued to rise, the reaction mixture became clear light-green and then turned to dark again. A solution of compound (8), 1-O, 2-O-dioctadecynyl-3-O-benzylglycerol (1.02 g, 1.5 mmol) in xylene (40 mL) was dripped into the heated xylene solution by syringe pump (50 mL syringe) over a period of 4–5 h. Following completion of the addition, heat and oxygen were turned off. Xylene was removed by rotoevaporation, 10% hydrochloric acid (150 mL) was added to the residue, and the mixture then extracted with ethyl acetate (3×100 mL). The combined ethyl acetate phases were washed with saturated sodium bicarbonate, water (3×), brine, and dried over sodium sulfate. Rotoevaporation of the ethyl acetate gave a residue which was purified by silica gel (400 mesh) chromatography, eluting with hexane-ethyl acetate (6:1 v/v) to give the macrocyclic product 9 (0.78 g, 77 percent yield). The yield is based on the amount of material recovered after purification by column chromatography.

Example 2

Repeating the procedure of Example 1, a 32 atom diether (79 percent yield) and 36 atom diether (83 percent yield) were prepared utilizing 1-O, 2-O-ditetradecyl-3-O-benzylglycerol and 1-O, 2-O-dihexadecyl-3-O-benzylglycerol as starting materials respectively.

Example 3

Formation of 72 atom tetraether giant ring, (compound 10)

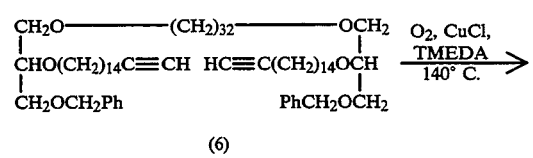

(6)

-continued $$\begin{array}{c} CH_2O \text{———} (CH_2)_{32} \text{———} OCH_2 \\ | \quad\quad\quad\quad\quad\quad\quad\quad\quad\quad\quad\quad | \\ CHO(CH_2)_{14}C\equiv C\text{——}C\equiv C(CH_2)_{14}OCH \\ | \quad\quad\quad\quad\quad\quad\quad\quad\quad\quad\quad\quad | \\ CH_2OCH_2Ph \quad\quad\quad\quad\quad PhCH_2OCH_2 \end{array}$$

(10)

To a three-neck, 500 mL round bottom flask containing 200 mL xylene and equipped as described in Example 1 were added 0.79 g (0.63 mmol) of 6, 156 mg (1.6 mmol, 2.5 equiv.) cuprous chloride and 248 μL (1.64 mmol, 2.6 equiv.) TMEDA. The mixture was then subjected to the same process as in Example 1 and the resulting product extracted with chloroform rather than ethyl acetate. The residue obtained after rotoevaporation of the solvent was purified by silica gel chromatography, eluting with hexane-ethyl acetate (10:1 v/v) to give 0.40 g (51% yield) giant ring tetraether 10 characterized as follows.

$^1$H NMR: (300 MHz, CDCl$_3$, CDCl$_3$=7.26 ppm ): 7.34 (m, 10H), 4.55 (s, 4H), 3.41–3.61 (m, 18H), 2.24 (t, J=6.9 Hz, 4H), 1.55 (m, 12H), 1.26 (s, 96H).

$^{13}$C NMR: (75.1 MHz, CDCl$_3$, CDCl$_3$=77.00 ppm): 138.42, 127.56, 127.48, 77.97, 73.34, 71.60, 71.01, 70.60, 70.29, 65.29, 30.08, 29.72, 29.62, 29.45, 29.09, 28.82, 28.33, 26.12, 26.09, 19.20.

Example 4

Formation of a 64 atom tetraether giant ring (compound 11)

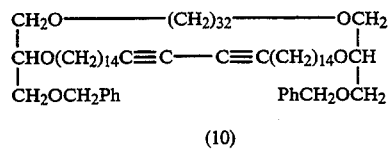

(7)

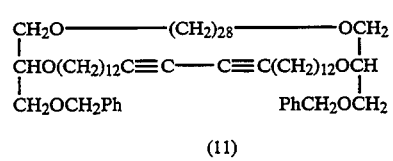

(11)

Following the procedure of Example 3, 0.38 g (0.33 mmol) of 7, 83 mg (0.83 mmol, 2.5 equiv.) cuprous chloride and 131 μL (0.87 mmol, 2.6 equiv.) TMEDA were reacted to give 0.25 g (66% yield) of a giant ring tetraether 11 characterized as follows.

$^1$H NMR: (300 MHz, CDCl$_3$, CDCl$_3$=7.26 ppm): 7.33 (m, 10H), 4.55 (s, 4H), 3.58 (m, 18H), 2.24 (t, J=6.6 Hz, 4H), 1.55 (m, 12H), 1.26 (s, 80H).

$^{13}$C NMR: (75.1 MHz, CDCl$_3$, CDCl$_3$=77.00 ppm): 138.41, 128.28, 127.55, 127.47, 77.98, 73.34, 71.58, 71.05, 70.58, 70.28, 65.29, 30.07, 29.61, 29.57, 29.44, 29.08, 28.81, 28.33, 26.11, 26.07, 19.19.

Example 5

Hydrogenation

A solution of the diacetylenic tetraether (0.22 g) obtained in Example 4 in THF-ethanol (10 mL, 4:1 v/v) was hydrogenated in the presence of 10% Palladium-carbon (0.11 g) at atmospheric pressure and 50° C. for a half hour. The mixture was filtered and washed with hot chloroform. After evaporating solvents, the crude product was recrystallized from hexane-ethanol (1:1 v/v) to yield 0.094 g (50%) of the saturated tetraether 11 characterized by low resolution fast atom bombardment mass spectrometry (LRFABMS) as follows.

LRFABMS(3-NBA): 971.8 (M+Li)+.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A giant ring compound of the Formula

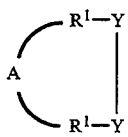
(I)

-continued

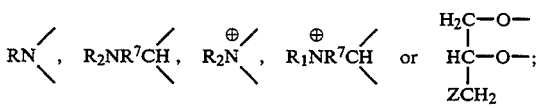

each $R^1$ is independently a $C_8$-$C_{40}$ backbone alkylene, alkenylene, alkynylene, alkadiynylene, or $(CHR^5CHR^5-O-)_n$;

each Y is independently —C≡C—, —C=C—, or —CH$_2$—CH$_2$—;

each R independently is hydrogen or $C_1$-$C_8$ alkyl;

$R^7$ is $(CH_2)_q$ where q is an integer from 1 to 4; and

Z is independently —OH, $C_{1-8}$ alkoxy, O-benzyl O-phosphate, O-glucose-sulfate or ZH=W where W is a phosphatidylethanolamine phosphatidylserine, phosphatidyl choline, phosphatidyl inositol, phosphatidyl ethanol trimethylamine, phosphatidic acid or a sugar moiety.

2. The composition of claim 1 wherein Z is phosphatidyl choline and $R^1$ is a $C_{12}$, $C_{14}$, or $C_{16}$ alkylene.

* * * * *

UNITED STATES PATENT AND TRADEMARK OFFICE
CERTIFICATE OF CORRECTION

PATENT NO. : 5,391,726  
DATED : February 21, 1995  
INVENTOR(S) : Fredric M. Menger Page 1 of 2

It is certified that error appears in the above-identified patent and that said Letters Patent is hereby corrected as shown below:

On the title page, item [56] add the following references:

| | | |
|---|---|---|
| 3,052,734 | 6/4/62 | Adams et al. |
| 3,207,804 | 9/21/65 | Adams et al. |
| 3,296,321 | 1/3/67 | Adams et al. |
| 4,136,098 | 1/23/79 | Burzin et al. |
| 4,413,154 | 11/1/83 | Dessau |
| 4,665,247 | 5/12/87 | Dessau |

<u>FOREIGN PATENT DOCUMENTS</u>

2,213,479   8/16/89   GB

UNITED STATES PATENT AND TRADEMARK OFFICE
CERTIFICATE OF CORRECTION

PATENT NO. : 5,391,726
DATED : February 21, 1995
INVENTOR(S) : Fredric M. Menger It is certified that error appears in the above-identified patent and that said Letters Patent is hereby corrected as shown below:

Claim 1, Column 12, lines 1-5, 4th formula, "$R_1NR^7CH$" should read -- $R_3NR^7CH$ --

Claim 1, Column 12, line 9, "$(CHR5CHR5-O-)_n$" should read --$(OCHR5\ CHR5)_n$--

Signed and Sealed this

Seventeenth Day of March, 1998

BRUCE LEHMAN

Attest:

Attesting Officer

Commissioner of Patents and Trademarks